United States Patent [19]

Daviduk et al.

[11] 3,998,899
[45] Dec. 21, 1976

[54] METHOD FOR PRODUCING GASOLINE FROM METHANOL

[75] Inventors: Nicholas Daviduk, Pennington; Michael T. Siuta, Trenton, both of N.J.

[73] Assignee: Mobil Oil Corporation, New York, N.Y.

[22] Filed: Aug. 6, 1975

[21] Appl. No.: 602,487

[52] U.S. Cl. ............... 260/668 R; 260/676 MS
[51] Int. Cl.² ............................. C07C 1/20
[58] Field of Search ....... 260/668 R, 668 A, 668 D, 260/676, 674, 614 R; 208/89

[56] References Cited
UNITED STATES PATENTS

| | | | |
|---|---|---|---|
| 3,036,134 | 5/1962 | Mattox | 260/614 R |
| 3,429,804 | 2/1969 | Sze et al. | 208/89 |
| 3,639,497 | 2/1972 | Martel et al. | 260/674 SE |
| 3,775,499 | 11/1973 | Debus et al. | 260/668 A |
| 3,930,812 | 1/1976 | Harris et al. | 260/449 M |

Primary Examiner—Veronica O'Keefe
Attorney, Agent, or Firm—C. A. Huggett; M. G. Gilman; C. D. Farnsworth

[57] ABSTRACT

A method for converting lower alcohols to ethers and hydrocarbons in an exothermic restricted process control arrangement with efficient utilization of process generated heat is described.

8 Claims, 1 Drawing Figure

METHOD FOR PRODUCING GASOLINE FROM METHANOL

The work described in this application was completed under contract with the United States Government, Office of Coal Research.

BACKGROUND OF THE INVENTION

U.S. Pat. No. 3,036,134 discloses the conversion of methanol to a reaction product containing water and dimethyl ether in the presence of a crystalline aluminosilicate. Copending application Ser. No. 387,223, filed Aug. 9, 1973, now U.S. Pat. No. 3,894,107, discloses the conversion of a reactant stream comprising alcohols and lower aliphatic organic compounds to a reaction product containing water and gasoline boiling range hydrocarbons containing aromatics by contacting the reactants with a special class of crystalline aluminosilicates. Some recently issued patents of interest are U.S. Pat. Nos. 3,702,886 issued Nov. 14, 1972 and 3,709,979 issued Jan. 9, 1973.

The conversion operations above identified perform exceptionally well at converting various oxygenated organic chemicals to gasoline boiling hydrocarbons. These conversions are exothermic to varying degrees depending on the particular reactant composition. While it is desirable under some circumstances to process exothermic reactions, large exothermic heat loads can require substantial investment in complex reactors with extensive cooling means thereby considerably detracting from the overall economic efficiency of the operation. Thus, the simple expedient of conducting the exothermic reactions in stages, spreads the self accelerating reactions into more easily controlled operations whereby the generated exothermic heat may be more efficiently utilized and dissipated.

SUMMARY OF THE INVENTION

This invention relates to the method and system for converting methanol to gasoline boiling components. More particularly, the present invention relates to the sequential restructuring of methanol through a plurality of catalyst contact zones temperature restrained in response to catalyst activity and selectivity. The invention relates to accomplishing the sequential restructuring of vaporized methanol first to ether and then to aromatics and isoparaffins boiling in the gasoline boiling range. In another aspect, the present invention relates to the method and combination of processing steps for catalytically restricting the conversion of methanol and the exothermic temperature rise encountered in the restructuring operation to formed ether as well as formed isoparaffin and aromatic components during contact with catalyst compositions suitable for such conversion.

In the operation contemplated by the present invention, the large amount of heat released during the conversion of methanol to gasoline boiling component is controlled in a sequentially arranged fixed catalyst bed system. The methanol feed is vaporized and converted initially to a mixture of dimethyl ether, methanol and water by contact with a suitable mass of catalyst, such as, gamma alumina wherein the reaction heat generated amounts to within the range of about 15 to 20% of the total heat release for the complete conversion of the methanol charge to gasoline boiling components. This initial reaction heat so generated is released essentially under self-limiting conditions since the reaction step is catalytically limited. The initial conversion of the methanol feed with the alumina catalyst acts to further heat the reactant by the partial conversion reaction heat and bring the resultant reactant stream to a temperature sufficiently high to initiate the subsequent conversion thereof to gasoline boiling range aromatics upon contact with a ZSM-5 type crystalline zeolite. In this combination of operating restraints, it has been found desirable to dilute the effluent from the gamma alumina conversion step with a light hydrocarbon gas comprising $C_5$ and lower boiling hydrocarbons which are used primarily as a heat sink and carrier to remove the remaining generated exothermic heat during the crystalline zeolite contact step. Water may also be used for this purpose but the use of additional amounts of water is considered a less desirable diluent material for reasons herein expressed. In the combination operation above described, the maximum temperature variation or increment in the crystalline catalyst system will be maintained within carefully controlled limits thereby enhancing the combination to which the present invention is directed.

The conversion of methanol to gasoline boiling components is a highly exothermic reaction releasing approximately 750 BTU of heat per pound of methanol. This amount of heat release will result in an adiabatic temperature increase of about 1200° F. for pure methanol feed. In an adiabatic catalyst bed reactor, this large temperature increase will result in high catalyst aging rates, and possibly cause thermal damage to the catalyst. Furthermore, such high temperatures could cause an undesirable product distribution to be obtained. Therefore, it is critical to the conversion of methanol to useful products to provide sufficient heat removing or dissipating facilities particularly during initial contact with the crystalline zeolite conversion catalyst so that the maximum temperature encountered in any portion of the zeolite catalyst conversion step is below an upper predetermined limit.

It is clear from the above brief discussion that a combination of at least two separate reaction temperature control mechanisms are relied upon and used in the combination of this invention. These temperature control mechanisms include a selective self-limiting catalyst relied upon to promote the conversion of methanol to dimethyl ether and thus partially heat the reactant to an elevated temperature suitable for the further conversion of a reactant product thereof with a ZSM-5 type crystalline zeolite to components boiling in the gasoline boiling range. The other temperature control mechanism particularly employed is directly to using a heat dissipating gasiform material in combination with the reactant charge passed to the crystalline zeolite conversion step. Thus, the present invention relies upon the use of light hydrocarbon gases, $C_5$ and lower boiling material alone or in combination with the water product of the initial conversion step to dilute the ether product effluent before contacting the ZSM-5 zeolite catalyst. By using a proper dilution ratio, the exothermic temperature rise in the ZSM-5 catalyst system is readily controlled within desired practical limits. The light hydrocarbon gases thus employed are easily separated from the higher boiling gasoline boiling components and can be recycled to the reactor inlet as diluent as provided above. In the event that water is used alone as a diluent it may be separated in a low pressure separator downstream of the reactor and recycled as herein discussed.

The catalyst systems contemplated in the combination process of the present invention are selected from catalyst compositions particularly promoting the sequence of conversion steps herein defined. Thus, it is proposed to use in the initial methanol conversions step, a selective catalyst composition which will restrict the conversion of methanol to an ether and thus its exothermic temperature rise. Preferably the catalyst should release only a portion of the total exothermic heat resulting from the conversion of methanol to gasoline boiling components. A catalyst suitable for this purpose in the ether forming step in gamma alumina. The crystalline zeolite conversion catalyst relied upon to convert the dimethyl ether product formed from the methanol charge and any unconverted methanol in the ether containing effluent is preferably a ZSM-5 crystalline zeolite material. However, other crystalline zeolites providing activity-selectivity characteristics similar to ZSM-5 crystalline zeolite such as ZSM-5 type materials comprising ZSM-11, ZSM-12, ZSM-21 and TEA mordenite may be employed.

The special zeolite catalysts referred to herein utilize members of a special class of zeolites exhibiting some unusual properties. These zeolites induce profound transformations of aliphatic hydrocarbons to aromatic hydrocarbons in commercially desirable yields and are generally highly effective in alkylation, isomerization, disproportionation and other reactions involving aromatic hydrocarbons. Although they have unusually low alumina contents, i.e. high silica to alumina ratios, they are very active even with silica to alumina ratios exceeding 30. This activity is surprising since catalytic activity of zeolites is generally attributed to framework aluminum atoms and cations associated with these aluminum atoms. These zeolites retain their crystallinity for long periods in spite of the presence of steam even at high temperatures which induce irreversible collapse of the crystal framework of other zeolites, e.g. of the X and A type. Furthermore, carbonaceous deposits, when formed, may be removed by burning at higher than usual temperatures to restore activity. In many environments, the zeolites of this class exhibit very low coke forming capability, conducive to very long times on stream between burning regenerations.

An important characteristic of the crystal structure of this class of zeolites is that it provides constrained access to, and egress from, the intra-crystalline free space by virtue of having a pore dimension greater than about 5 Angstroms and pore windows of about a size such as would be provided by 10-membered rings of oxygen atoms. It is to be understood, of course, that these rings are those formed by the regular disposition of the tetrahedra making up the anionic framework of the crystalline aluminosilicate, the ocygen atoms themselves being bonded to the silicon or aluminum atoms at the centers of the tetrahedra. Briefly, the preferred zeolites useful as catalysts in this invention possess, in combination: a silica to alumina ratio of at least about 12; and a structure providing constrained access to the crystalline free space.

The silica to alumina ratio referred to may be determined by conventional analysis. This ratio is meant to represent, as closely as possible, the ratio in the rigid anionic framework of the zeolite crystal and to exclude aluminum in the binder or in cationic or other form within the channels. Although zeolites with a silica to alumina ratio of at least 12 are useful, it is preferred to use zeolites having higher ratios of at least about 30.

Such zeolites, after activation, acquire an intracrystalline sorption capacity for normal hexane which is greater than that for water, i.e. they exhibit "hydrophobic" properties. It is believed that this hydrophobic character is advantageous in the present invention.

The zeolites useful as catalysts in this invention freely sorb normal hexane and have a pore dimension greater than about 5 Angstroms. In addition, their structure must provide constrained access to some larger molecules. It is sometimes possible to judge from a known crystal structure whether such constrained access exists. For example, if the only pore windows in a crystal are formed by 8-membered rings of oxygen atoms, then access by molecules of larger cross-section than normal hexane is substantially excluded and the zeolite is not of the desired type. Zeolites with windows of 10-membered rings are preferred, although excessive puckering or pore blockage may render these zeolites substantially ineffective. Zeolites with windows of twelve-membered rings do not generally appear to offer sufficient constraint to produce the advantageous conversions desired in the instant invention, although structures can be conceived, due to pore blockage or other cause, that may be operative.

Rather than attempt to judge from crystal structure whether or not zeolite possesses the necessary constrained access, a simple determination of the "constraint index" may be made by continuously passing a mixture of equal weight of normal hexane and 3-methylpentane over a small sample, approximately 1 gram or less, of zeolite at atmospheric pressure according to the following procedure. A sample of the zeolite, in the form of pellets or extrudate, is crushed to a particle size about that of coarse sand and mounted in a glass tube. Prior to testing, the zeolite is treated with a stream of air at 1000° F for at least 15 minutes. The zeolite is then flushed with helium and the temperature adjusted between 550° F and 950° F to give an overall conversion between 10% and 60%. The mixture of hydrocarbons is passed at 1 liquid hourly spaced velocity (i.e., 1 volume of liquid hydrocarbon per volume of catalyst per hour) over the zeolite with a helium dilution to give a helium to total hydrocarbon mole ratio of 4:1. After 20 minutes on stream, a sample of the effluent is taken and analyzed, most conveniently by gas chromatography, to determine the fraction remaining unchanged for each of the two hydrocarbons.

The constraint index is calculated as follows:

$$\text{Constraint Index} = \frac{\log_{10} \text{(fraction of n-hexane remaining)}}{\log_{10} \text{(fraction of 3-methylpentane remaining)}}$$

The constraint index approximates the ratio of the cracking rate constants for the two hydrocarbons. Catalysts suitable for the present invention are those which employ a zeolite having a constraint index from 1.0 to 12.0. Constraint Index (CI) values for some typical zeolites including some not within the scope of this invention are:

| CAS | C.I. |
|---|---|
| ZSM-5 | 8.3 |
| ZSM-11 | 8.7 |
| ZSM-35 | 4.5 |
| TMA Offretite | 3.7 |
| ZSM-12 | 2 |
| ZSM-38 | 2 |

| CAS | C.I. |
| --- | --- |
| Beta | 0.6 |
| ZSM-4 | 0.5 |
| Acid Mordenite | 0.5 |
| REY | 0.4 |
| Amorphous Silica-alumina | 0.6 |
| Erionite | 38 |

The above-described Constraint Index is an important and even critical, definition of those zeolites which are useful to catalyze the instant process. The very nature of this parameter and the recited technique by which it is determined, however, admit of the possibility that a given zeolite can be tested under somewhat different conditions and thereby have different constraint indexes. Constraint Index seems to vary somewhat with severity of operation (conversion). Therefore, it will be appreciated that it may be possible to so select test conditions to establish multiple constraint indexes for a particular given zeolite which may be both inside and outside the above defined range of 1 to 12.

Thus, it should be understood that the Constraint Index value as used herein is an inclusvie rather than an exclusive value. That is, a zeolite when tested by any combination of conditions within the testing definition set forth herein above to have a constraint index of 1 to 12 is intended to be included in the instant catalyst definition regardless that the same identical zeolite tested under other defined conditions may give a constraint index value outside of 1 to 12.

The class of zeolites defined herein is exemplified by ZSM-5, ZSM-11, ZSM-12, ZSM-21, ZSM-35, ZSM-38 and other similar material. Recently issued U.S. Pat. No. 3,702,886 describing and claiming ZSM-5 is incorporated herein by reference.

ZSM-11 is more particularly described in U.S. Pat. No. 3,709,979, the entire contents of which are incorporated herein by reference.

ZSM-12 is more particularly described in U.S. Pat. No. 3,832,449, the entire contents of which are incorporated herein by reference.

U.S. application, Ser. No. 358,192, filed May 7, 1973, now abandoned, the entire contents of which are incorporated herein by reference, describes a zeolite composition, and a method of making such, designated as ZSM-21 which is useful in this invention.

U.S. application Ser. No. 528,061 filed Nov. 29, 1974, the entire contents of which are incorporated herein by reference, describes a zeolite composition including a method of making it. This composition is designated ZSM-35 and is useful in this invention.

U.S. application Ser. No. 528,060, filed Nov. 29, 1974, the entire contents of which are incorporated herein by reference, describes a zeolite composition including a method of making it. This composition is designated ZSM-38 and is useful in this invention.

The x-ray diffraction pattern of ZSM-21 appears to be generic to that of ZSM-35 and ZSM-38. Either or all of these zeolites is considered to be within the scope of this invention.

The specific zeolites described, when prepared in the presence of organic cations, are substantially catalytically inactive, possibly because the intracrystalline free space is occupied by organic cations from the forming solution. They may be activated by heating in an inert atmosphere at 1000° F for 1 hour, for example, followed by base exchange with ammonium salts followed by calcination at 1000° F in air. The presence of organic cations in the forming solution may not be absolutely essential to the formation of this special type zeolite; however, the presence of these cations does appear to favor the formation of this special type of zeolite. More generally, it is desirable to activate this type zeolite by base exchange with ammonium salts followed by calcination in air at about 1000° F for from about 15 minutes to about 24 hours.

Natural zeolites may sometimes be converted to this type zeolite by various activation procedures and other treatments such as base exchange, steaming, alumina extraction and calcination, alone or in combinations. Natural minerals which may be so treated include ferrierite, brewsterite, stilbite, dachiardite, epistilbite, heulandite and clinoptilolite. The preferred crystalline aluminosilicates are ZSM-5, ZSM-11, ZSM-12 and ZSM-21, with ZSM-5 particularly preferred.

The zeolites used as catalysts in this invention may be in the hydrogen form or they may be base exchanged or impregnated to contain ammonium or a metal cation complement. It is desirable to calcine the zeolite after base exchange. The metal cations that may be present include any of the cations of the metals of Groups I through VIII of the periodic table. However, in the case of Group IA metals, the cation content should in no case be so large as to substantially eliminate the activity of the zeolite for the catalysis being employed in the instant invention. For example, a completely sodium exchanged H-ZSM-5 appears to be largely inactive for shape selective conversions required in the present invention.

In a preferred aspect of this invention, the zeolites useful as catalysts herein are selected as those having a crystal framework density, in the dry hydrogen form, of not substantially below about 1.6 grams per cubic centimeter. It has been found that zeolites which satisfy all three of these criteria are most desired. Therefore, the preferred catalysts of this invention are those comprising zeolites having a constraint index as defined above of about 1 to 12, a silica to alumina ratio of at least about 12 and a dried crystal density of not substantially less than about 1.6 grams per cubic centimeter. The dry density for known structures may be calculated from the number of silicon plus aluminum atoms per 1000 cubic Angstroms, as given, e.g., on page 19 of the article on Zeolite Structure by W. M. Meier, This paper, the entire contents of which are incorporated herein by reference, is included in "Proceedings of the Conference on Molecular Sieves, London, April, 1967" published by the Society of Chemical Industry, London, 1968. When the crystal structure is unknown, the crystal framework density may be determined by classical pyknometer techniques. For example, it may be determined by immersing the dry hydrogen form of the zeolite in an organic solvent which is not sorbed by the crystal. It is possible that the unusual sustained activity and stability of this class of zeolites is associated with its high crystal anionic framework density of not less than about 1.6 grams per cubic centimeter. This high density of course must be associated with a relatively small amount of free space within the crystal, which might be expected to result in more stable structures. This free space, however, seems to be important as the locus of catalytic activity.

Crystal framework densities of some typical zeolites including some which are not within the purview of this invention are:

| Zeolite | Void Volume | Framework Density |
|---|---|---|
| Ferrierite | 0.28 cc/cc | 1.76 g/cc |
| Mordenite | .28 | 1.7 |
| ZSM-5, −11 | .29 | 1.79 |
| Dachiardite | .32 | 1.72 |
| L | .32 | 1.61 |
| Clinoptilolite | .34 | 1.71 |
| Laumontite | .34 | 1.77 |

-continued

| Zeolite | Void Volume | Framework Density |
|---|---|---|
| ZSM-4 (Omega) | .38 | 1.65 |
| Heulandite | .39 | 1.69 |
| P | .41 | 1.57 |
| Offretite | .40 | 1.55 |
| Levynite | .40 | 1.54 |
| Erionite | .35 | 1.51 |
| Gmelinite | .44 | 1.46 |
| Chabazite | .47 | 1.45 |
| A | .5 | 1.3 |
| Y | .48 | 1.27 |

| STREAM | MW | SG | 6<br>CRUDE METHANOL | 16<br>DME REACTOR EFFLUENT | 54<br>GAS RECYCLE | 24<br>M-GASO REACTOR EFFLUENT |
|---|---|---|---|---|---|---|
| BPSD | | | 100 | | | |
| MSCFD | | | | 384.5 | 1232.1 | 1673.1 |
| LB/HR | | | 1205 | 1205 | 2980 | 4185 |
| API OR SG at 60° F | | | .840 | | | |
| MW | | | 28.5 | 28.5 | 22.0 | 22.8 |
| GPM | | | 2.92 | | | |
| CFM | | | | 29.0 | 54.7 | 161.7 |
| COMPONENT | MW | SG | | | | |
| $H_2$ | | | | | 41.78 | 41.89 |
| $C_1$ | | | | | 43.85 | 44.12 |
| CO | | | | | 2.70 | 2.71 |
| $CO_2$ | | | | | 1.43 | 1.45 |
| $C_2=$ | | | | | 1.01 | 1.03 |
| $C_2$ | | | | | 11.69 | 11.90 |
| $C_3=$ | | | | | 2.44 | 2.55 |
| $C_3$ | | | | | 17.10 | 17.37 |
| $iC_4$ | | | | | 5.74 | 6.42 |
| $C_4=$ | | | | | 1.87 | 2.14 |
| $nC_4$ | | | | | 2.06 | 2.39 |
| $C_5$'s | 71.5 | .636 | | | 2.44 | 3.42 |
| $C_6$'s | 85.6 | .675 | | | .53 | 1.13 |
| $C_7$'s | 99.1 | .702 | | | .09 | .33 |
| $C_8$'s | 113.0 | .732 | | | .03 | .17 |
| $C_9$'s | 127.2 | .746 | | | | .05 |
| $C_{10}$'s | 142.3 | .734 | | | | .01 |
| & BENZENE | 78.1 | .835 | | | .02 | .05 |
| TOLUENE | 92.1 | .872 | | | .06 | .26 |
| $C_8$ AROM | 106.2 | .872 | | | .06 | .61 |
| $C_9$ AROM | 120.2 | .876 | | | .02 | .39 |
| $C_{10}$ AROM | 134.0 | .832 | | | | .14 |
| $C_{11}$ AROM | 145.2 | .921 | | | | .02 |
| METHANOL | 32.0 | .792 | 31.58 | 7.30 | | |
| DIMETHYL ETHER | 46.1 | — | | 12.14 | | |
| $H_2O$ | | | 10.69 | 22.83 | .54 | 42.77 |
| TOTAL MPH | | | 42.27 | 42.27 | 135.46 | 183.92 |

| STREAM | MW | SG | 52<br>SEPARATOR VAPOR | 70<br>SEPARATOR LIQUID | 48<br>SEPARATOR WATER | 80<br>SEPARATOR OFF-GAS |
|---|---|---|---|---|---|---|
| BPSD | | | | | | |
| MSCFD | | | 1235.0 | 44.9 | 52.2 | 2.5 |
| LB/HR | | | 2987 | 438 | 760 | 7 |
| API OR SG at 60° F | | | | .669 | 1.000 | |
| MW | | | 22.0 | 73.7 | 18.0 | 22.0 |
| GPM | | | | 1.35 | 1.55 | |
| CFM | | | 54.8 | | | .1 |
| COMPONENT | MW | SG | | | | |
| $H_2$ | | | 41.87 | .02 | | .09 |
| $C_1$ | | | 43.94 | .18 | | .09 |
| CO | | | 2.71 | | | .01 |
| $CO_2$ | | | 1.44 | .01 | | .01 |
| $C_2=$ | | | 1.01 | .02 | | |
| $C_2$ | | | 11.71 | .19 | | .02 |
| $C_3=$ | | | 2.44 | .11 | | |
| $C_3$ | | | 17.13 | .84 | | .03 |
| $iC_4$ | | | 5.75 | .67 | | .01 |
| $C_4=$ | | | 1.88 | .26 | | .01 |
| $nC_4$ | | | 2.07 | .32 | | .01 |
| $C_5$'s | 71.5 | .636 | 2.44 | .98 | | |
| $C_6$'s | 85.6 | .675 | .53 | .60 | | |
| $C_7$'s | 99.1 | .702 | .09 | .24 | | |
| $C_8$'s | 113.0 | .732 | .03 | .14 | | |
| $C_9$'s | 127.2 | .746 | | .05 | | |
| $C_{10}$'s | 142.3 | .734 | | .01 | | |
| BENZENE | 78.1 | .835 | .02 | .03 | | |
| TOLUENE | 92.1 | .872 | .06 | .20 | | |
| $C_8$ AROM | 106.2 | .872 | .06 | .55 | | |
| $C_9$ AROM | 120.2 | .876 | .02 | .37 | | |
| $C_{10}$ AROM | 134.0 | .832 | | .14 | | |

-continued

| | | | | | | |
|---|---|---|---|---|---|---|
| C₁₁ AROM | 145.2 | .921 | | .02 | | |
| METHANOL | 32.0 | .792 | | | TRACE | |
| DIMETHYL ETHER | 46.1 | — | | | | |
| H₂O | | | .54 | .01 | 42.22 | |
| TOTAL MPH | | | 134.74 | 5.96 | 42.22 | .28 |

| STREAM | | | 94 STABILIZER OVHD | 102 STABILIZER OFF-GAS | 104 STABILIZER+ REFLUX | 86 STABILIZER BOTTOMS |
|---|---|---|---|---|---|---|
| BPSD | | | | | 58.9 | 29.3 |
| MSCFD | | | 106.7 | 25.5 | | |
| LB/HR | | | 603 | 126 | 477 | 319 |
| API OR SG at 60° F | | | | | .558 | .747 |
| MW | | | 51.4 | 44.5 | 53.6 | 93.6 |
| GPM | | | | | 1.88 | 1.08 |
| CFM | | | 5.9 | 1.5 | | |
| COMPONENT | MW | SG | | | | |
| H₂ | | | .11 | .11 | | |
| C₁ | | | .33 | .27 | .06 | |
| CO | | | .01 | .01 | | |
| CO₂ | | | .02 | .02 | | |
| C₂= | | | .02 | .02 | | |
| C₂ | | | .39 | .21 | .18 | |
| C₃= | | | .33 | .11 | .22 | |
| C₃ | | | 2.86 | .87 | 1.99 | |
| iC₄ | | | 3.81 | .66 | 3.15 | .02 |
| C₄= | | | 1.64 | .25 | 1.39 | .02 |
| nC₄ | | | 2.04 | .28 | 1.76 | .05 |
| C₅'s | 71.5 | .636 | .17 | .01 | .16 | .97 |
| C₆'s | 85.6 | .675 | | | | .60 |
| C₇'s | 99.1 | .702 | | | | .24 |
| C₈'s | 113.0 | .732 | | | | .14 |
| C₉'s | 127.2 | .746 | | | | .05 |
| C₁₀'s | 142.3 | .734 | | | | .01 |
| & BENZENE | 78.1 | .835 | | | | .03 |
| TOLUENE | 92.1 | .872 | | | | .20 |
| C₈ AROM | 106.2 | .872 | | | | .55 |
| C₉ AROM | 120.2 | .876 | | | | .37 |
| C₁₀ AROM | 134.0 | .832 | | | | .14 |
| C₁₁ AROM | 145.2 | .921 | | | | .02 |
| METHANOL | 32.0 | .792 | | | | |
| DIMETHYL ETHER | 46.1 | — | | | | .01 |
| H₂O | | | | | | |
| TOTAL MPH | | | 11.73 | 2.82 | 8.91 | 3.42 |

| STREAM | | | 68 HYDROCARBON QUENCH | 26 EFFLUENT VS. METHANOL | 28 EFFLUENT VS. RECYCLE GAS |
|---|---|---|---|---|---|
| BPSD | | | 188.6 | | |
| MSCFD | | | | 836.5 | 836.5 |
| LB/HR | | | 1844 | 2092 | 2092 |
| API OR SG at 60° F | | | .669 | | |
| MW | | | 73.7 | 22.0 | 22.0 |
| GPM | | | 5.67 | | |
| CFM | | | | 80.8 | 80.8 |
| COMPONENT | MW | SG | | | |
| H₂ | | | .10 | 20.95 | 20.95 |
| C₁ | | | .74 | 22.06 | 22.06 |
| CO | | | .01 | 1.36 | 1.36 |
| CO₂ | | | .06 | .72 | .72 |
| C₂= | | | .05 | .51 | .51 |
| C₂ | | | .78 | 5.95 | 5.95 |
| C₃= | | | .44 | 1.27 | 1.27 |
| C₃ | | | 3.52 | 8.98 | 8.98 |
| iC₄ | | | 2.81 | 3.21 | 3.21 |
| C₄= | | | 1.11 | 1.07 | 1.07 |
| nC₄ | | | 1.36 | 1.20 | 1.20 |
| C₅'s | 71.5 | .636 | 4.11 | 1.71 | 1.71 |
| C₆'s | 85.6 | .675 | 2.53 | .57 | .57 |
| C₇'s | 99.1 | .702 | 1.01 | .16 | .16 |
| C₈'s | 113.0 | .732 | .62 | .08 | .08 |
| C₉'s | 127.2 | .746 | .21 | .03 | .03 |
| C₁₀'s | 142.3 | .734 | .05 | .01 | .01 |
| & BENZENE | 78.1 | .835 | .13 | .03 | .03 |
| TOLUENE | 92.1 | .872 | .84 | .13 | .13 |
| C₈ AROM | 106.2 | .872 | 2.31 | .30 | .30 |
| C₉ AROM | 120.2 | .876 | 1.56 | .19 | .19 |
| C₁₀ AROM | 134.0 | .832 | .56 | .07 | .07 |
| C₁₁ AROM | 145.2 | .921 | .08 | .01 | .01 |
| METHANOL | 32.0 | .792 | | | |
| DIMETHYL ETHER | 46.1 | — | | | |
| H₂O | | | .05 | 21.39 | 21.39 |
| TOTAL MPH | | | 25.04 | 91.96 | 91.96 |

The table above identifies various processing streams hereinafter discussed.

Figure 1:
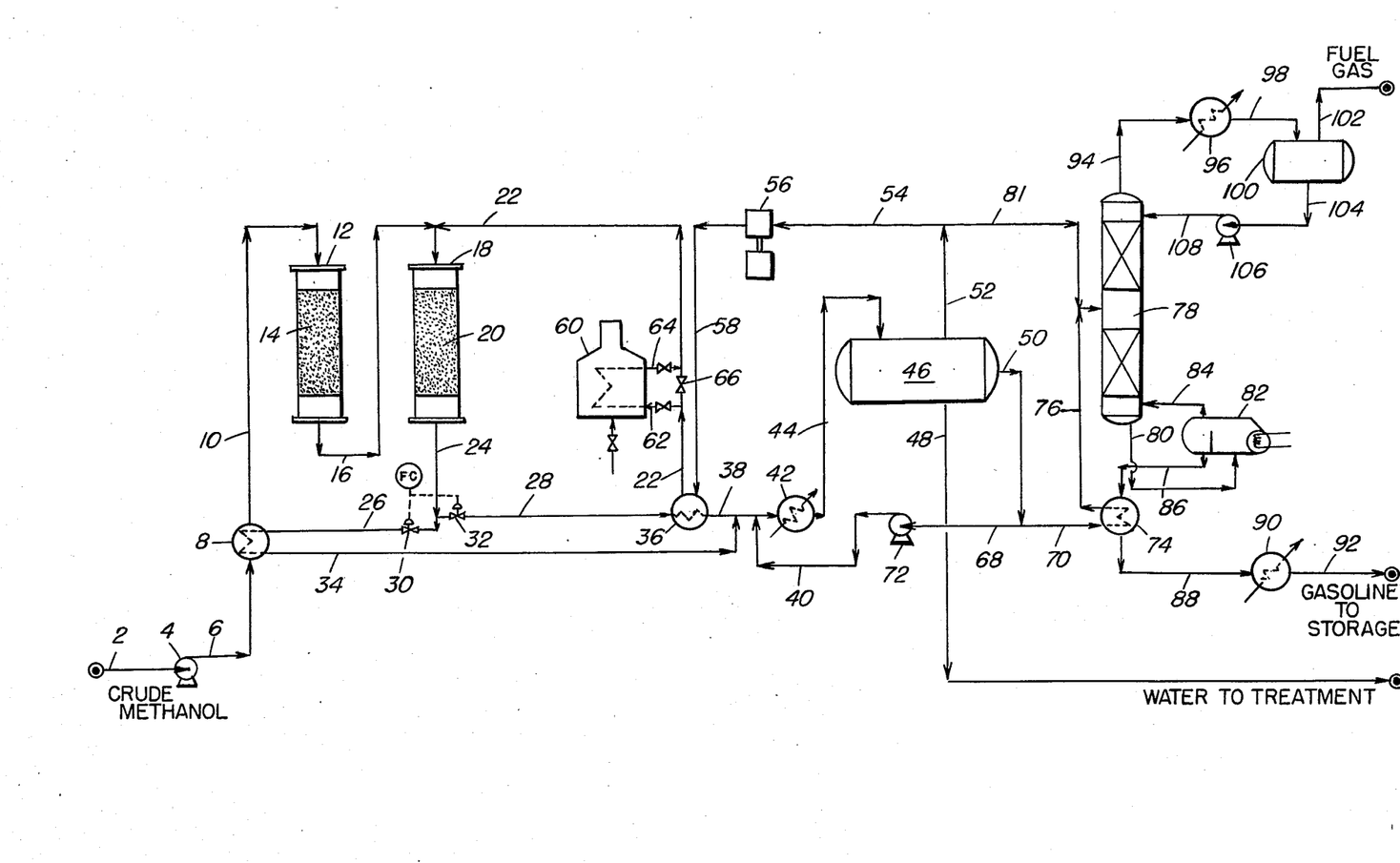
The drawing is a diagrammatic sketch in elevation of a processing arrangement for converting the lower alcohols, $C_1$ to $C_3$ alcohols in a sequential catalyst arrangement maintained under restricted exothermic reaction conditions particularly promoting the formation of gasoline boiling range hydrocarbons comprising aromatics.

Referring now to the drawing by way of example, an alcohol feed such as crude methanol and identified in the above table is introduced to the process by conduit 2 to a pump 4 wherein the pressure of the methanol feed is raised to about 335 psig. The, thus, pressurized feed at a temperature of about 100° F is passed by conduit 6 to a heat exchanger train represented by means 8 wherein the temperature of the feed is raised to about 600° F by indirect heat exchange with a portion of the product effluent of the ether conversion step obtained as hereinafter described. The methanol fuel at a temperature of about 600° F and an elevated pressure of about 305 psig is passed by conduit 10 to reactor 12 having a gamma alumina condensation catalyst 14. The condensation catalyst may be any catalyst suitable for the purpose of changing the lower alcohol feed to particularly corresponding ether products and water which particularly catalystically restricts the exothermicity of the reaction and generated heat rise of the product effluent thereof.

The aliphatic organic intermediate product comprising ethers in admixture with unreached alcohols and water formed in the process is then passed at an elevated temperature of about 770° F by conduit 16 to a second reaction zone 18 containing a bed of catalyst 20. Recycled gasiform material hereinafter identified and at a temperature of about 615° F and an elevated pressure in conduit 22 is admixed with that in conduit 16 to form a mixture at a temperature of about 650°. The composition of the reactor effluent in conduit 16 and the recycle steam in conduit 22 is identified in the table. The mixture is then passed in contact with catalyst bed 20 comprising a crystalline zeolite selected from the class of crystalline zeolites represented by ZSM-5 crystalline zeolite (crystalline aluminosilicate). In the reaction stage of zone 18 and catalyst 20, the conversion of the intermediate product and unconverted alcohol material to gasoline boiling hydrocarbons and aromatics is accomplished under exothermic conditions raising the temperature of the reaction products up to about 850° F. The diluent effect of this recycle gas stream and the water content of product effluent of the first reaction zone 12 operate to provide restrictions on the exothermic heat rise encountered in the second reaction zone 18. The hydrocarbon containing product effluent of zone 18 is withdrawn by conduit 24 at a temperature of about 850° F and separated into two streams 26 and 28 controlled by valves 30 and 32 respectively. Temperature modulated flow control means are provided in association with valves 30 and 32. In this arrangement, a sufficient amount of the 850° F product effluent of zone 18 is passed by conduit 26 to indirect heat exchange means 8 to provide the heat duty required therein to preheat and raise the temperature of alcohol feed from about 100° F up to about 600° F. The effluent stream thus cooled is withdrawn from heat exchange means 8 by conduit 34 at a temperature of about 265° F and processed as discussed below.

The hot effluent portion withdrawn by conduit 28 and controlled by valve 32 is passed in indirect heat exchange with recycle gasiform material thereby heating the recycle gas to an elevated temperature of about 615° F and thereby cooling the effluent passed therethrough to about 265° F. The thus cooled effluent is then recovered by conduit 38, combined with the cooled effluent in conduit 33, quenched to a temperature of about 230° F. by a quench fluid in conduit 40 before entering cooler 42. In heat exchanger or cooler 42, the hydrocarbon containing effluent is further cooled to a temperature of about 100° F before passing by conduit 44 to a knock out of separation drum 46.

In separator drum 46 maintained at a temperature of about 100° F and a pressure of about 225 psig, a rough separation is made to provide a water phase withdrawn by conduit 48, a hydrocarbon phase withdrawn by conduit 50 and a gaseous phase withdrawn by conduit 62 hereinbefore referred to as recycle gasiform material recycled by conduit 22. The recycle gaseous material of a composition identified in the table is recycled in part by conduit 54 to compressor 56 wherein the pressure of the recycle gas is raised to about 300 psig. The compressed recycle gas is passed by conduit 58 to heat exchanger means 36 wherein its temperature is raised to about 615° F. The heated recycle gas is then passed by conduit 22 to reactor 18 as above discussed. During start up of the process, a furnace 60 is provided with connecting conduits 62 and 64 with suitable valve means for controlling and passing recycled flue gas through the furnace 60 to heat it to a temperature sufficient for recycle to reactor 18.

The hydrocarbon phase withdrawn from drum 46 by conduit 50 is separated into two streams 68 and 70. Stream 68 is passed to pump 72 and thence by conduit 40 as quench fluid for admixture with the effluent in conduit 38 and 34. The remaining portion of the effluent comprising stream 70 is passed to a heat exchanger 74 wherein the temperature of this stream is indirectly heated to a temperature of about 200° F and withdrawn therefrom by conduit 76 for passage to a stabilizer tower 78. Recycle gas withdrawn from separator 46 by conduit 52 in excess of that recycled by conduit 54 is passed by conduit 81 to the stabilizer tower 78. The stabilizer tower 78 is maintained at a bottom pressure of about 165 psig and a top pressure of about 160 psig. A gasoline product fraction is withdrawn from the bottom of the stabilizer tower by conduit 80 and passed to a reboiler 82 wherein its temperature is raised to about 345° F. A portion of the thus heated gasoline fraction is returned by conduit 84 to the bottom portion of the stabilizer tower 78. The remaining portion of the heated gasoline fraction is passed by conduit 86 to heat exchanger 74 wherein it gives up heat to the hydrocarbon stream in conduit 70 passed to heat exchanger 74. In exchanger 74, the gasoline product fraction is cooled to about 190° F before by conduit 88 to cooler 90 wherein its temperature is reduced to about 100° F. The temperature reduced gasoline product fraction is then passed by conduit 92 to storage and/or gasoline blending facilities not shown.

An overhead fraction comprising primarily $C_4$ and lower boiling components is withdrawn from the upper portion of the stabilizer tower by conduit 94 at a temperature of about 155° F. The material in conduit 94 is cooled in cooler 96 before passage by conduit 98 to separator drum 100 maintained at a temperature of about 125° F and a pressure of about 155 psig. In separator drum 100, a fuel gas portion is recovered and withdrawn therefrom by conduit 102. A liquid reflux fraction is separated and withdrawn by conduit 104 for passage to pump 106 and conduit 108 to the upper portion of the stabilizer tower 78.

The water phase separated in drum 46 and withdrawn by conduit 48 is passed to water treatment not shown.

Having thus generally described the processing combination of the present invention and described a specific embodiment in support thereof, it is to be understood that no undue restrictions are to be imposed by reason thereof except as defined by the following claims.

We claim

1. In a process for converting $C_1$ to $C_3$ alcohols to gasoline boiling range products by the combination of initially forming ether products of the alcohol fuel in a first catalyst stage followed by conversion of the ether product to gasoline boiling products in a second stage with a crystalline zeolite selected from the class of zeolites represented by ZSM-5 crystalline zeolite, the comprised method for utilizing exothermic heat generated by the process which comprises separating a product effluent stream recovered from the crystalline zeolites conversion stage into two elevated temperature product streams, passing one of said elevated temperature product effluent streams in indirect heat exchange with alcohol fuel being passed to said first catalyst stage in an amount sufficient to raise the temperature of the alcohol fuel up to reaction temperature and recovering a first product stream therefrom of considerably reduced temperature;

passing another of said product effluent streams in indirect heat exchange with a recycle gas stream recovered as hereinafter provided in an amount sufficient to raise the temperature of the recycle gas suitable for passage to said crystalline zeolite catalyst stage thereby providing a second product stream of considerably reduced temperature;

combining said first and second product streams of considerably reduced temperature, further cooling said combined product streams sufficient to permit recovery of a recycle gas stream, a liquid hydrocarbon phase comprising gasoline boiling component and a water phase, recycling said recovered recycle gas to the heat exchange step above recited after compression thereof and separating said liquid hydrocarbon phase under conditions to recover gasoline boiling components from lower boiling fuel gas components.

2. In a process for catalytically converting lower alcohol to ethers and thereafter to hydrocarbons including gasoline boiling range hydrocarbons, the improvement which comprises, recovering and separating a hot product effluent of said combination into two streams, using one of said streams to indirectly preheat said alcohol fuel stream passed to said contact conversion step, using the other of said hot product effluent streams to indirectly preheat recycle gas passed to the other conversion step of the process, recovering a product effluent stream from each of said indirect heat exchange step of substantially reduced temperature, further cooling and separating in a first separation zone said combined product effluent stream into a recycle gas stream, a water rich phase and hydrocarbon rich phase comprising gasoline boiling hydrocarbons, passing separated recycle gas to said recycle gas indirect heat exchange step and separating said hydrocarbon rich phase to recover gasoline boiling hydrocarbons.

3. The process of claim 2 wherein the conversion of alcohols to ethers is substantially catalytically restricted and conversion of the ethers to gasoline boiling hydrocarbons is accomplished with one of a special class of cystalline zeolites represented by ZSM-5.

4. The process of claim 2 wherein a portion of the separated hydrocarbon phase is combined with product effluent obtained from said heat exchange steps as a quench fluid before further cooling and separation of said combined product effluent stream.

5. The process of claim 2 wherein a portion of the separated hydrocarbon rich phase is reheated by indirect heat exchange with stabilized gasoline product before passage to a hydrocarbon product stabilization zone.

6. The process of claim 5 wherein a portion of the recycle gas stream is passed to said stabilization zone maintained at a pressure below the pressure at which the recycle gas is separated from the hydrocarbon rich phase and said water phase in said first separation zone.

7. The process of claim 2 wherein, during start up of the process, the passed through said indirect heat exchange zone recycle gas is passed through a downstream furnace zone to raise the temperature of the recycle gas to a temperature suitable for use in said ether conversion step.

8. In a process for converting alcohols to ethers in a first stage and ethers to gasoline boiling hydrocarbons with a crystalline zeolite catalyst in a second stage, the improvement which comprises, directing the product effluent of said zeolite conversion with first and second product effluent streams, using said first product effluent stream to indirectly preheat the alcohol fuel passed to said first catalyst stage, using said second product stream to preheat a recycle gas stream passed to said second zeolite catalyst conversion stage, recovering first and second product effluent streams of reduced temperature from said indirect heat exchange steps as a conbined stream, cooling the combined product effluent stream by addition of a quench fluid thereto before further indirect cooling therefore, separating the cooled product effluent at an elevated pressure into a recycle gas stream phase, a hydrocarbon product phase and a water phase, recycling a portion of said recycle gas phase, using a portion of said hydrocarbon product phase as quench fluid and separating the remaining portion of said hydrocarbons product phase to recover gasoline boiling hydrocarbons.

* * * * *

UNITED STATES PATENT AND TRADEMARK OFFICE
CERTIFICATE OF CORRECTION

PATENT NO. : 3,998,899                  PAGE 1 of 2

DATED : December 21, 1976

INVENTOR(S) : NICHOLAS DAVIDUK and MICHAEL T. SIUTA

It is certified that error appears in the above—identified patent and that said Letters Patent are hereby corrected as shown below:

Column 2, Line 51.    "directly" should read -- directed --

Column 3, Line 5.    "conversions" should read -- conversion --

Column 3, Line 12.    "in" should read -- is -- (second occurrence)

Column 3, Line 54.    "ocygen" should read -- oxygen --

Column 4, Line 26.    Change "whether or not zeolite" to -- whether or not a zeolite --

Column 4, Line 33.    "particule" should read -- particle --

Column 4, Line 49.    insert quotes around "constraint index"

Column 5, Lines 26 & 27.    insert quotes around "constraint index"

Columns 7 & 8, last table.    lined up incorrectly as:
```
"BPSD
  MSCFD     1235.0     44.9     52.2     2.5"
```
should be:
```
-- BPSD                 44.9     52.2
   MSCFD    1235.0                        2.5 --
```

Columns 9 & 10, second table.    lined up incorrectly as:
```
"dimethyl ether    46.1    -             .01
 H2O                                         "
```
should be:
```
-- dimethyl ether   46.1    -
   H2O                                    .01 --
```

UNITED STATES PATENT AND TRADEMARK OFFICE
CERTIFICATE OF CORRECTION

PATENT NO. : 3,998,899
DATED : December 21, 1976
INVENTOR(S) : NICHOLAS DAVIDUK and MICHAEL T. SIUTA It is certified that error appears in the above–identified patent and that said Letters Patent are hereby corrected as shown below:

Column 11, Line 34.  "650°" should read -- 650°F --

Column 11, Line 36.  "steam" should read -- stream --

Column 12, Line 52.  after the word "before" insert the word -- passage --

Signed and Sealed this

Eighth Day of March 1977

[SEAL]

Attest:

RUTH C. MASON
*Attesting Officer*

C. MARSHALL DANN
*Commissioner of Patents and Trademarks*